(12) United States Patent
Radgowski et al.

(10) Patent No.: US 11,317,977 B2
(45) Date of Patent: May 3, 2022

(54) SURGICAL INSTRUMENT WITH COMMONLY ACTUATED ROBOTIC AND MANUAL FEATURES

(71) Applicant: INTUITIVE SURGICAL OPERATIONS, INC., Sunnyvale, CA (US)

(72) Inventors: Todd J. Radgowski, San Francisco, CA (US); Craig Tsuji, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 138 days.

(21) Appl. No.: 16/892,578

(22) Filed: Jun. 4, 2020

(65) Prior Publication Data
US 2020/0330169 A1 Oct. 22, 2020

Related U.S. Application Data

(63) Continuation of application No. 16/139,242, filed on Sep. 24, 2018, now Pat. No. 10,716,636, which is a
(Continued)

(51) Int. Cl.
*A61B 34/30* (2016.01)
*A61B 17/00* (2006.01)

(52) U.S. Cl.
CPC .... *A61B 34/30* (2016.02); *A61B 2017/00477* (2013.01); *A61B 2218/007* (2013.01)

(58) Field of Classification Search
CPC .... A61B 2017/00477; A61B 2218/007; A61B 34/30
See application file for complete search history.

(56) References Cited

U.S. PATENT DOCUMENTS 2,812,765 A 11/1957 Tofflemire
3,814,249 A 6/1974 Eaton
(Continued)

FOREIGN PATENT DOCUMENTS

WO   WO-2011002215 A2   1/2011

OTHER PUBLICATIONS

Advisory Action dated Mar. 20, 2009 for U.S. Appl. No. 11/341,004, filed Jan. 27, 2006 (ISRG00050/US).
(Continued)

*Primary Examiner* — Jonathan T Kuo
(74) *Attorney, Agent, or Firm* — Haynes and Boone, LLP

(57) ABSTRACT

A method for using a surgical instrument comprises actuating a movable valve member at a first time using robotic action and actuating the valve member at a second time using manual action. The instrument comprises the valve member, a robotic actuation piece, a chassis, a transport shaft coupled to the chassis, a cavity extending through the transport shaft, and a valve. The chassis is adapted to be mated with a robotic manipulator. The valve comprises the valve member, a manual button coupled thereto, and a valve channel. The valve member is configured to translate across the valve channel along an axis. Robotic actuation comprises rotating the robotic actuation piece around an axis perpendicular to the axis of the valve member. Manual action comprises translating the manual button parallel to the axis of the valve member. The robotic actuation piece remains engaged with the valve member during the manual action.

20 Claims, 12 Drawing Sheets

Related U.S. Application Data continuation of application No. 13/446,978, filed on Apr. 13, 2012, now Pat. No. 10,098,703.

(60) Provisional application No. 61/524,241, filed on Aug. 16, 2011.

(56) References Cited

U.S. PATENT DOCUMENTS

| | | |
|---|---|---|
| 4,299,221 A | 11/1981 | Phillips et al. |
| 4,369,785 A | 1/1983 | Rehkopf et al. |
| 4,370,983 A | 2/1983 | Lichtenstein |
| 4,397,640 A | 8/1983 | Haug et al. |
| 4,596,374 A | 6/1986 | Thompson et al. |
| 4,668,215 A | 5/1987 | Allgood |
| 4,755,168 A | 7/1988 | Romanelli et al. |
| 4,873,943 A | 10/1989 | Pulvermacher |
| 5,071,412 A | 12/1991 | Noda |
| 5,078,140 A | 1/1992 | Kwoh |
| 5,100,377 A | 3/1992 | Freitas et al. |
| 5,380,280 A | 1/1995 | Peterson |
| 5,429,596 A | 7/1995 | Arias et al. |
| 5,460,604 A | 10/1995 | Arnett et al. |
| 5,472,432 A | 12/1995 | Martin |
| 5,484,402 A | 1/1996 | Saravia et al. |
| 5,605,537 A | 2/1997 | Ivey |
| 5,685,821 A | 11/1997 | Pike |
| 5,697,898 A | 12/1997 | Devine |
| 5,836,909 A | 11/1998 | Cosmescu |
| 5,902,264 A | 5/1999 | Toso et al. |
| 5,906,591 A | 5/1999 | Dario et al. |
| 5,931,808 A | 8/1999 | Pike |
| 5,941,867 A | 8/1999 | Kao |
| 6,004,509 A | 12/1999 | Dey et al. |
| 6,148,857 A | 11/2000 | West et al. |
| 6,149,622 A | 11/2000 | Marie |
| 6,234,205 B1 | 5/2001 | Damelio et al. |
| 6,279,595 B1 | 8/2001 | Walrath et al. |
| 6,331,181 B1 | 12/2001 | Tierney et al. |
| 6,610,059 B1 | 8/2003 | West, Jr. |
| 6,689,146 B1 | 2/2004 | Himes |
| 6,817,974 B2 | 11/2004 | Cooper et al. |
| 6,860,878 B2 | 3/2005 | Brock |
| 10,098,703 B2 | 10/2018 | Radgowski et al. |
| 2002/0072736 A1 | 6/2002 | Tierney et al. |
| 2002/0188279 A1 | 12/2002 | Waddell et al. |
| 2003/0090909 A1 | 5/2003 | Kalkbrenner |
| 2003/0167056 A1 | 9/2003 | Jahns et al. |
| 2003/0176766 A1 | 9/2003 | Long et al. |
| 2003/0176767 A1 | 9/2003 | Long et al. |
| 2003/0216617 A1 | 11/2003 | Hirakui |
| 2003/0220609 A1 | 11/2003 | Childers et al. |
| 2004/0082915 A1 | 4/2004 | Kadan |
| 2004/0158203 A1 | 8/2004 | Cover et al. |
| 2004/0243147 A1 | 12/2004 | Lipow |
| 2005/0192532 A1 | 9/2005 | Kucklick et al. |
| 2006/0030840 A1 | 2/2006 | Nowlin et al. |
| 2006/0058617 A1 | 3/2006 | Sano et al. |
| 2006/0173403 A1 | 8/2006 | Injev |
| 2006/0178556 A1 | 8/2006 | Hasser et al. |
| 2007/0005002 A1 | 1/2007 | Millman et al. |
| 2007/0016174 A1 | 1/2007 | Millman et al. |
| 2007/0156121 A1 | 7/2007 | Millman et al. |
| 2008/0064921 A1 | 3/2008 | Larkin et al. |
| 2008/0065102 A1 | 3/2008 | Cooper |
| 2008/0065103 A1 | 3/2008 | Cooper |
| 2008/0086087 A1 | 4/2008 | Spohn et al. |
| 2009/0036740 A1 | 2/2009 | Finlay et al. |
| 2009/0088772 A1 | 4/2009 | Blumenkranz |
| 2009/0099520 A1 | 4/2009 | Millman |
| 2019/0021801 A1 | 1/2019 | Radgowski et al. |

OTHER PUBLICATIONS

Final Office Action dated Apr. 6, 2011 for U.S. Appl. No. 11/454,359, filed Jun. 15, 2006 (ISRG00053/US).
Final Office Action dated Jan. 7, 2010 for U.S. Appl. No. 11/341,004, filed Jan. 27, 2006 (ISRG00050/US).
Final Office Action dated Jul. 8, 2011 for U.S. Appl. No. 11/341,155, filed Jan. 27, 2006 (ISRG00051/US).
Final Office Action dated May 12, 2010 for U.S. Appl. No. 11/454,476, filed Jun. 15, 2006 (ISRG00052/US).
Final Office Action dated Jan. 16, 2009 for U.S. Appl. No. 11/341,004, filed Jan. 27, 2006 (ISRG00050/US).
Final Office Action dated Mar. 25, 2010 for U.S. Appl. No. 11/341,155, filed Jan. 27, 2006 (ISRG00051/US).
Final Office Action dated Jul. 29, 2011 for U.S. Appl. No. 11/341,004, filed Jan. 27, 2006 (ISRG00050/US).
Non-Finai Office Action dated Oct. 5, 2009 for U.S. Appl. No. 11/341,155, filed Jan. 27, 2006 (ISRG00051/US).
Non-Final Office Action dated Aug. 6, 2008 for U.S. Appl. No. 11/341,004, filed Jan. 27, 2006 (ISRG00050/US).
Non-Final Office Action dated Dec. 8, 2010 for U.S. Appl. No. 11/454,476, filed Jun. 15, 2006 (ISRG00052/US).
Non-Final Office Action dated Nov. 19, 2010 for U.S. Appl. No. 11/341,004, filed Jan. 27, 2006 (ISRG00050/US).
Non-Final Office Action dated Nov. 22, 2010 for U.S. Appl. No. 11/341,155, filed Jan. 27, 2006 (ISRG00051/US).
Non-Final Office Action dated Oct. 27, 2009 for U.S. Appl. No. 11/454,476, filed Jun. 15, 2006 (ISRG00052/US).
Non-Final Office Action dated Aug. 30, 2010 for U.S. Appl. No. 11/454,359, filed Jun. 15, 2006 (ISRG00053/US).
Non-Final Office Action dated Jul. 30, 2009 for U.S. Appl. No. 11/341,004, filed Jan. 27, 2006 (ISRG00050/US).
Pease, Dudely A., "Basic Fluid Power," 1967, pp. 136-190, Prentice-Hall inc.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

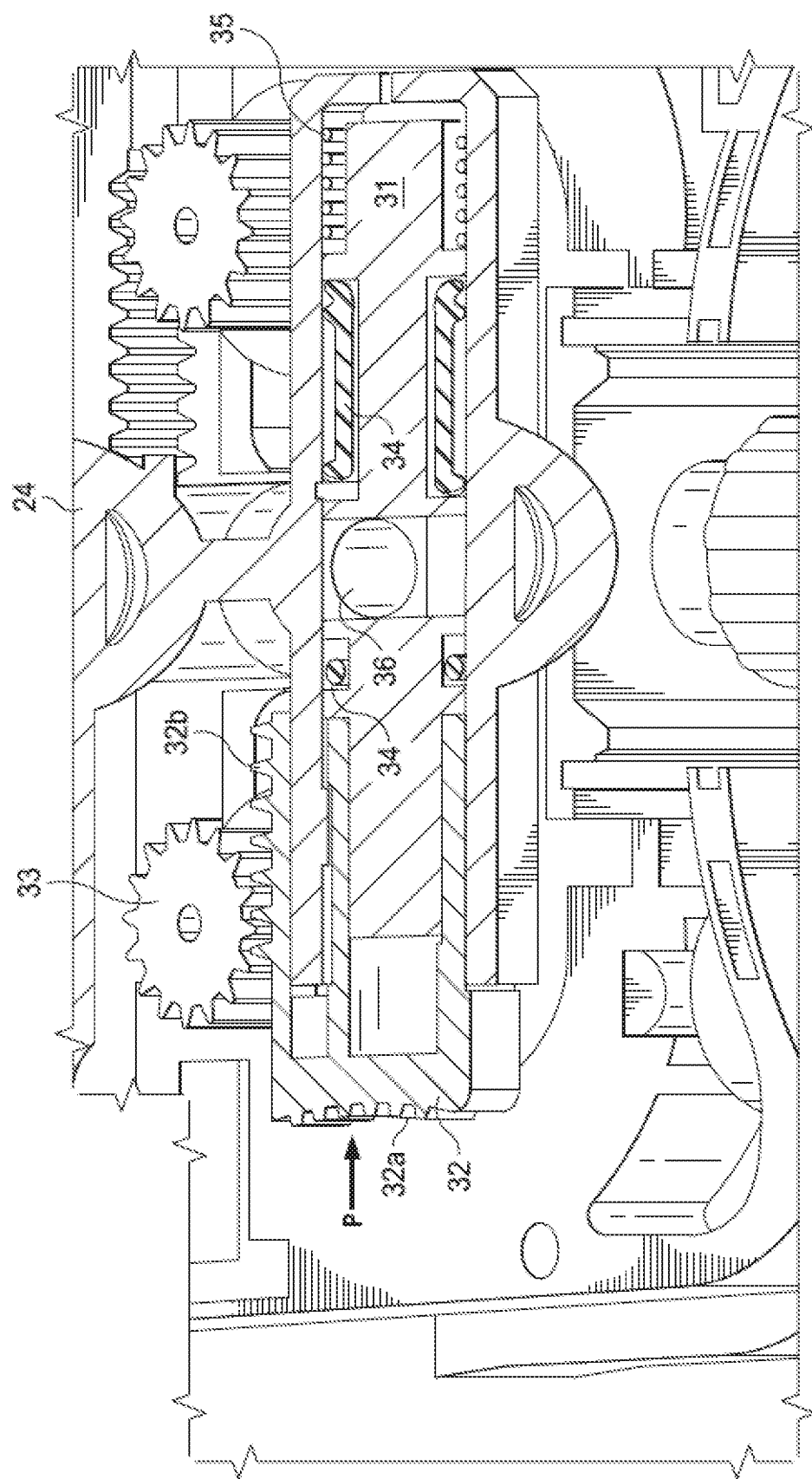

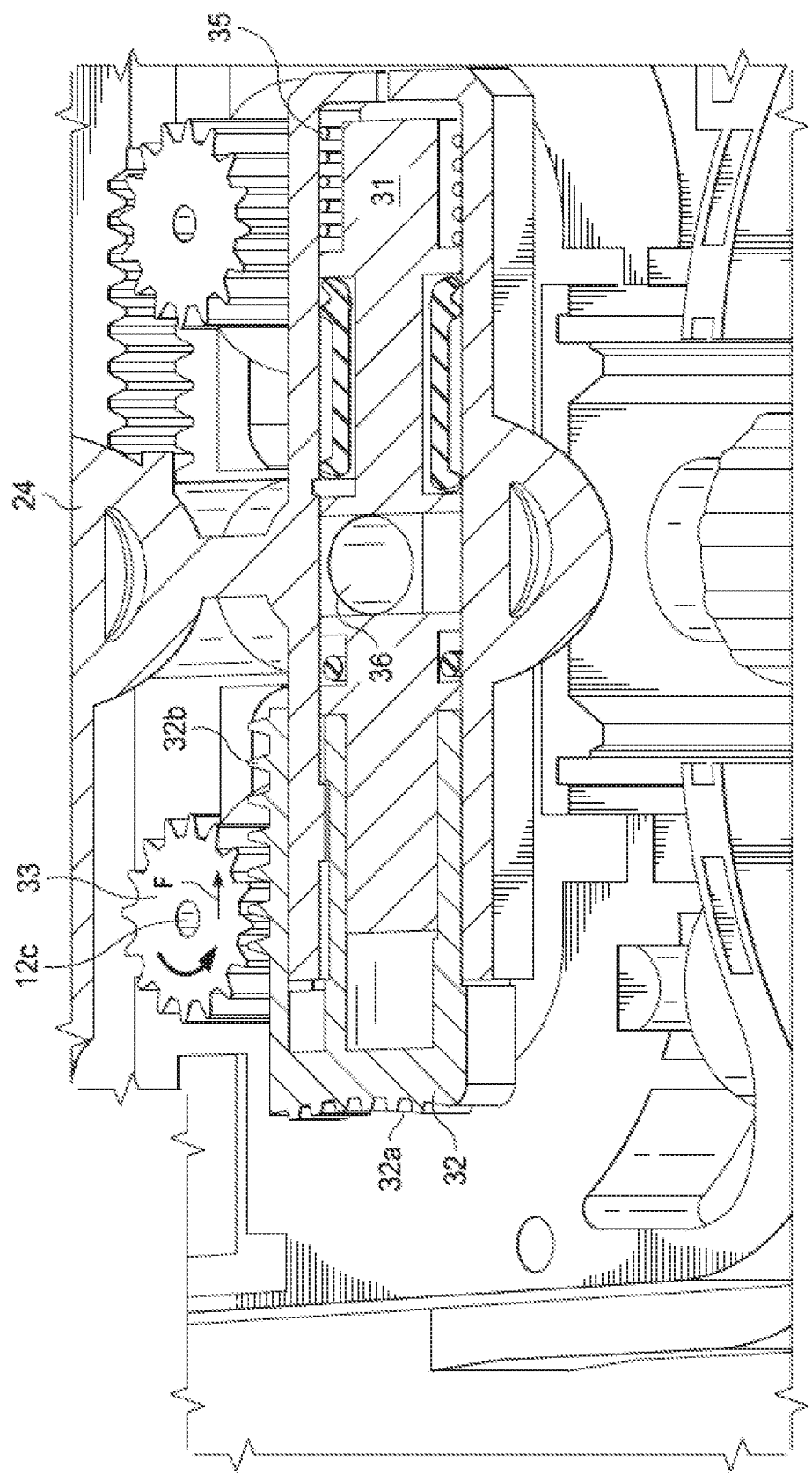

SURGICAL INSTRUMENT WITH COMMONLY ACTUATED ROBOTIC AND MANUAL FEATURES

CROSS-REFERENCE TO RELATED APPLICATIONS

This patent application is a continuation of U.S. patent application Ser. No. 16/139,242, filed Sep. 24, 2018, which is a continuation of U.S. patent application Ser. No. 13/446,978 (filed Apr. 13, 2012) and is related to and claims priority to U.S. Patent Application No. 61/524,241 (filed Aug. 16, 2011; entitled "Surgical Instrument with Commonly Actuated Robotic and Manual Features," by Radgowski et al.), the contents of each of which are incorporated herein by reference in their entirety and for all purposes.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

The present disclosure relates generally to surgical instruments, and more particularly to steerable and articulate surgical instruments having robotically actuated features and manually actuated features.

In the field of robotic surgery and machine-aided surgical procedures there is the need to rapidly and efficiently introduce material to, and remove material from, the surgical area. For example, in some situations it is desirable to remove blood accumulation near a surgical site in order to maintain good visibility for the surgeons. Similarly, it is desirable to remove smoke during endoscopic procedures to maintain good visibility. In some situations it is desirable to introduce a gas to inflate a body cavity that includes an organ or a tissue that is involved in surgery. Such insufflation provides sufficient space for the surgeon to move the surgical instruments and for an adequate endoscopic field of view. In other situations, it may be desirable to irrigate the surgical area (e.g., with water or a saline solution), either for allowing visibility of the area of interest or to provide moisture to the tissue surrounding the area of interest.

During teleoperated robotic surgery (e.g., using a da Vinci® Surgical System, commercialized by Intuitive Surgical, Inc., Sunnyvale, Calif.), teleoperated surgical instruments are introduced through the patient's body wall in order to access and work at a surgical site. In situations in which surgical suction or irrigation is required, a patient side surgical assistant removes one of the robotically controlled instruments from its associated cannula, and then manually introduces a manually controlled instrument that provides suction or irrigation. The assistant then manually maneuvers and operates the suction or irrigation instrument while viewing the surgical site in a patient side monitor, while at the same time coordinating with the surgeon, who is operating the master surgical system control. Once the patient side assistant completes the suction or irrigation function, the manual instrument is removed and the robotic surgical instrument replaced. Thus, the need to use manually operated suction and irrigation instruments for surgical procedures that involve a telerobotic surgical system interferes with the surgical work flow. This need also defeats some of the advantages of the camera-referenced telepresence that such a surgical system offers. Nevertheless, there are situations in which a manually operated suction or irrigation instrument is desirable during a telerobotic surgical procedure, such as controlling the suction and irrigation functions and suction/irrigation instrument position as the surgeon operates two other telerobotic surgical instruments.

What is needed is a surgical instrument that provides the benefit of both teleoperated surgical operation and the benefit of operation by a patient side assistant.

SUMMARY

According to embodiments disclosed herein, an instrument may include an end effector at a distal end, an actuator mechanism at a proximal end, the actuator mechanism including a first valve, a robotic control coupled to the first valve, and a manual control coupled to the first valve. The instrument may further include a transport shaft between the actuator mechanism and the end effector, the transport shaft including a cavity, coupled to the first valve, that facilitates material transport along the transport shaft, the first valve having an actuating axis perpendicular to a rotational axis of the robotic control.

Further according to embodiments disclosed herein, a method for using an instrument with actuated features may include actuating a first valve in a proximal end of the instrument to access a cavity included in a transport shaft of the instrument, wherein actuating the first valve includes: actuating an actuator mechanism that includes a robotic control coupled to the first valve and a manual control coupled to the first valve in response to activation of the robotic control or the manual control in a direction perpendicular to a rotational axis of the robotic control.

Further according to some embodiments disclosed herein, a method of using an instrument may include coupling a material source to a cavity in the instrument; coupling a suction source to the cavity in the instrument; and actuating a first valve coupled to the cavity to access the material source using an actuator mechanism including a robotic control coupled to the first valve and a manual control coupled to the first valve. The method may further include actuating a second valve coupled to the cavity to access the suction source using an actuator mechanism including a robotic control coupled to the second valve and a manual control coupled to the second valve.

BRIEF DESCRIPTION OF THE DRAWINGS

FIG. 7B illustrates a cross-sectional perspective view of a proximal end mechanism included in a surgical instrument according to some embodiments.

FIG. 7C illustrates a cross-sectional perspective view of a proximal end mechanism included in a surgical instrument according to some embodiments.

DETAILED DESCRIPTION

The present disclosure relates generally to surgical instruments, and more particularly to steerable and articulate surgical instruments having robotically actuated features and manually actuated features. The combination of manually and robotically actuated features provides flexibility for the use of surgical instruments according to the present disclosure. For example, a steering mechanism may be actuated with a robotic mechanism controlled by a specialized surgeon, and a valve for irrigating tissue or suction of material from tissue may be manually operated. In such situations, the valve may be operated once the steering mechanism has placed a distal end of the surgical instruments in a desirable location relative to the area of interest.

The present application is related to the following U.S. Patent Applications, all assigned to Intuitive Surgical Operations, Inc., the contents of which are incorporated herein by reference in their entirety and for all purposes: U.S. patent application Ser. No. 11/341,004 (filed Jan. 27, 2006; entitled "Robotic Surgical Instruments for Irrigation, Aspiration, and Blowing" by Millman et al.); U.S. patent application Ser. No. 11/341,155 (filed Jan. 27, 2006; entitled "Robotic Surgical Instruments with a Fluid Flow Control System for Irrigation, Aspiration, and Blowing" by Millman et al.); U.S. patent application Ser. No. 11/454,359 (filed Jun. 15, 2006; entitled "Robotic Surgical Systems with Fluid Flow Control for Irrigation, Aspiration, and Blowing" by Millman et al.); and U.S. patent application Ser. No. 11/454,476 (filed Jun. 15, 2006; entitled "Methods of Fluid Flow Control with Robotic Surgical Instruments for Irrigation, Aspiration, and Blowing" by Millman et al.).

Figure 1:
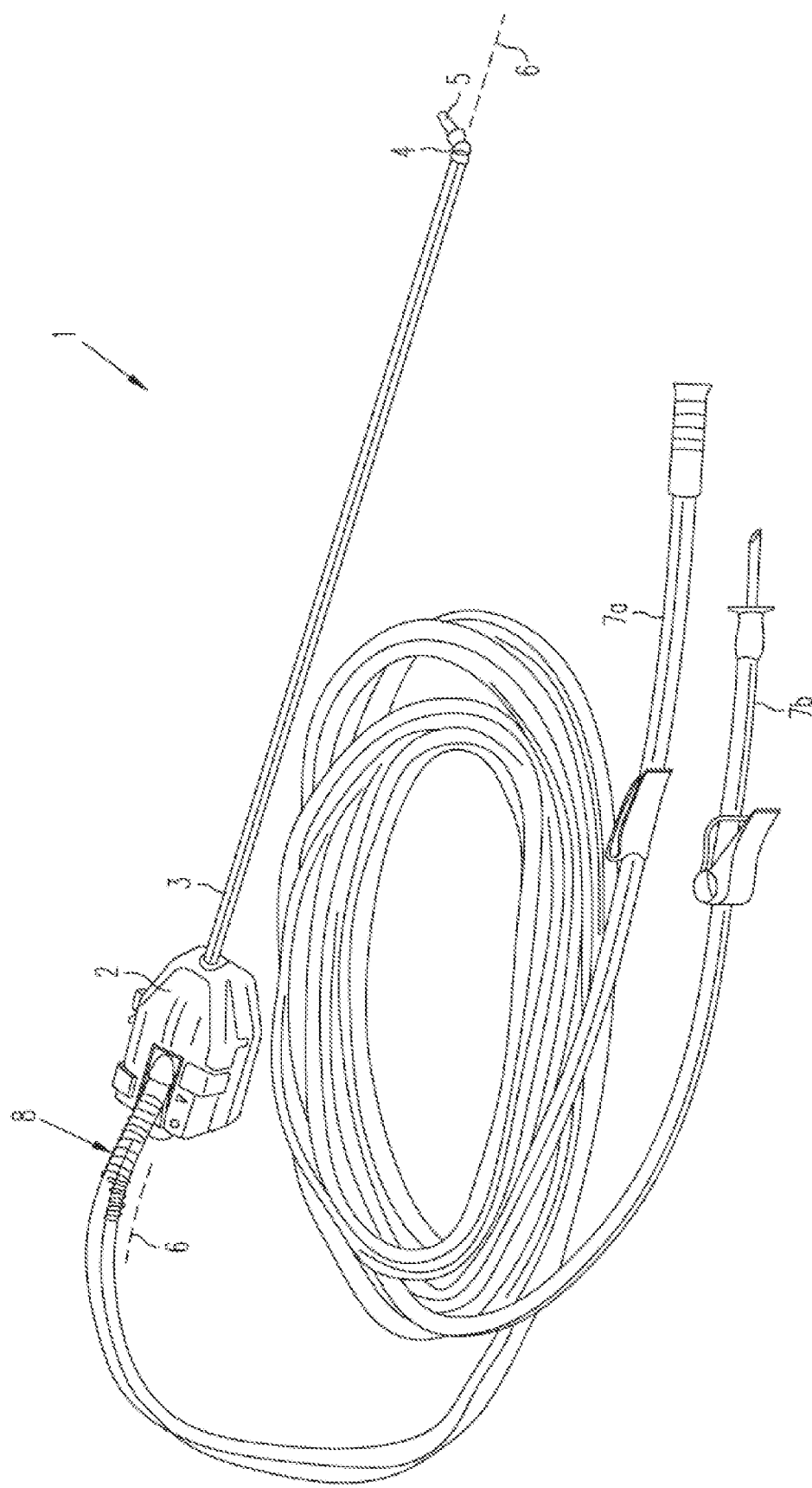
FIG. 1 illustrates a perspective view of a surgical instrument according to some embodiments.

FIG. 1 is a perspective view of a surgical instrument 1, according to some embodiments. Proximal and distal orientations are as shown by the arrows and are arbitrary terms. As shown in FIG. 1, surgical instrument 1 includes four portions: a proximal end mechanism 2, an elongate transport shaft 3, a wrist mechanism 4, and an end effector 5 at the distal end.

In the depicted embodiment, proximal end mechanism 2 is configured to be removably mated with a surgical robotic manipulator arm (not shown; e.g., a da Vinci® model IS3000 surgical system instrument manipulator arm commercialized by Intuitive Surgical, Inc. of Sunnyvale, Calif.). Components in proximal end mechanism 2 function as force transmission mechanisms to receive teleoperated servo actuation forces from the surgical robotic manipulator and in turn redirect the received forces to operate components of instrument 1, such as changing the orientation of wrist 4 and operating other components in proximal end mechanism 2, as described below. In the depicted embodiment, proximal end mechanism 2 receives four separate actuation inputs from its associated robotic manipulator. In other embodiments, proximal end mechanism 2 may be modified to receive more or fewer inputs from an associated manipulator, depending on the number of instrument 1 features to be controlled. In some embodiments, proximal end mechanism 2 may include one or more motors that operate associated instrument 1 features, and such motor(s) rather than an external actuator provides force to operate the associated feature. In the depicted embodiment, there is no input that controls transport shaft 3 roll, although such a feature (known in other da Vinci® surgical system instruments) may be included in other embodiments.

Transport shaft 3 couples proximal end mechanism 2 to end effector 5, so that end effector 5 can be inserted through a patient's body wall to reach a surgical site while proximal end mechanism 2 remains outside the patient. In the depicted embodiment, the outer diameter of transport shaft 3 is about 8 mm, although this dimension can be varied for other embodiments. In addition, in the depicted embodiment transport shaft 3 is substantially rigid, although in some embodiments transport shaft 3 may be flexible (see e.g., U.S. Patent Application Pub. No. U.S. 2011/0071544 A1 (filed Nov. 13, 2009; entitled "Curved Cannula Instrument"), assigned to Intuitive Surgical Operations, Inc., the contents of which are incorporated herein by reference in their entirety). For this description, a longitudinal axis 6 that runs along the centerline of transport shaft 3 is defined for instrument 1. Further according to some embodiments, transport shaft 3 may include a cavity that provides material transfer along the shaft. For example, material may be transferred between a distal end of transport shaft 3 and a proximal end of transport shaft 3. In some embodiments, the material transfer may take place between a point near the proximal end of transport shaft 3 and a point near the distal end of transport shaft 3.

As shown in FIG. 1, wrist mechanism 4 is coupled between the distal end of transport shaft 3 and end effector 5. Features of wrist mechanism 4 are described in more detail below. In the depicted embodiment, wrist mechanism 4 allows end effector 5 to change orientation with two degrees of freedom (DOFs), arbitrarily termed pitch and yaw, with reference to axis 6. In some embodiments, wrist 4 may enable only a single DOF (e.g., pitch or yaw). In some embodiments, wrist mechanism 4 may enable more than two DOFs so that compound curves can be controlled. In yet other embodiments, wrist mechanism 4 may be eliminated so that end effector 5 is directly connected to the distal end of transport shaft 3.

In some embodiments, a pitch degree of freedom and a yaw degree of freedom include angular motions (changes of orientation) within a plane arbitrarily oriented in three-dimensional (3-d) space. Furthermore, a pitch plane may be oriented perpendicularly to a yaw plane, according to some embodiments.

End effector 5 is described in more detail below. In the depicted embodiment, end effector 5 is configured to accommodate both an irrigation function and a suction function at a surgical site. Therefore, an enclosed channel forming a lumen extends from end effector 5, through wrist 4 and transport shaft 3, to proximal end mechanism 2, which controls whether the suction or irrigation function is enabled in instrument 1.

FIG. 1 also shows two connection features 7a and 7b. In the depicted embodiment, connection feature 7a is a flexible tube that couples a surgical irrigation fluid (liquid or gas) source (not shown) to instrument 1 so that irrigation fluid can be routed from a source through feature 7a, proximal end mechanism 2, transport shaft 3, and wrist 4 to exit via end effector 5. Similarly, connection feature 7b is a flexible tube that couples a surgical suction source (not shown) to instrument 1 so that matter from a surgical site can be drawn into end effector 5, and through wrist 4, transport shaft 3, proximal end mechanism 2, and connection feature 7b, to the source. In the depicted embodiment, optional metal coils 8 are positioned around connection features 7a,7b near proximal end mechanism 2 so as to prevent features 7a,7b from kinking. Other known anti-kink technology may be used in other embodiments.

Figure 2:
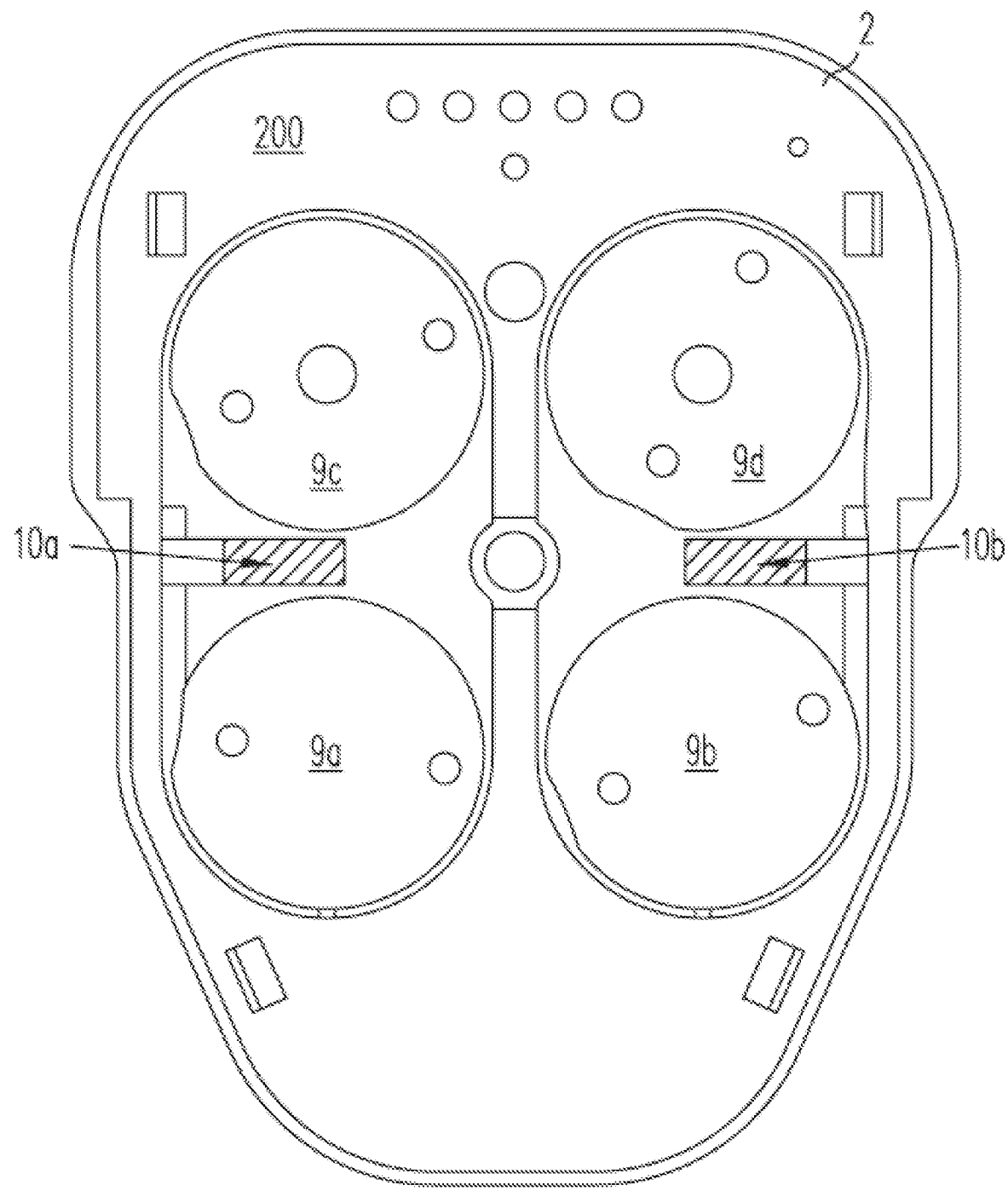
FIG. 2 illustrates a plan view of a proximal end mechanism according to some embodiments.

FIG. 2 is a plan view of proximal end mechanism 2, which shows the side 200, which mates with the robotic manipulator, according to some embodiments. In some embodiments, side 200 is coupled to a support platform for holding surgical instrument 1. Side 200 may be a supporting side of surgical instrument 1, according to embodiments disclosed herein. A supporting side of surgical instrument 1 is a side of the instrument that couples to a supporting arm in a robotic instrument or a holding platform for the instrument. In some embodiments, a supporting side of the instrument may be a side that rests directly on the hand of a user manually controlling the surgical instrument. As shown, four disks 9a-9d are mounted in proximal end mechanism 2, and each disk receives a unique input from an external servo-motor. Consistent with some embodiments, disks 9a-9d may be associated with wrist control, suction control, irrigation control, and roll control. According to one embodiment, disks 9a and 9b are associated with wrist 4 control, disk 9c is associated with control of the suction function, and disk 9d is associated with the irrigation function. Also shown are the ends of engagement latches 10a, and 10b, which when latched release instrument 1 from its associated robotic manipulator sterile interface feature. Latches 10a and 10b ensure a simple disengagement between disks 9a-9d and their associated drivers.

Further according to some embodiments, a roll motion of transport shaft 3 may be executed using one of disks 9a-9d. In such embodiments, a single disk may be used to control irrigation and suction valves. For example, by rotating a disk counter-clockwise, a suction valve may be opened and an irrigation valve may be closed; and by rotating the disk in a clockwise rotation an irrigation valve may be opened and a suction valve may be closed. Further, a neutral position of the controller may leave both irrigation and suction valves closed.

Figure 3:
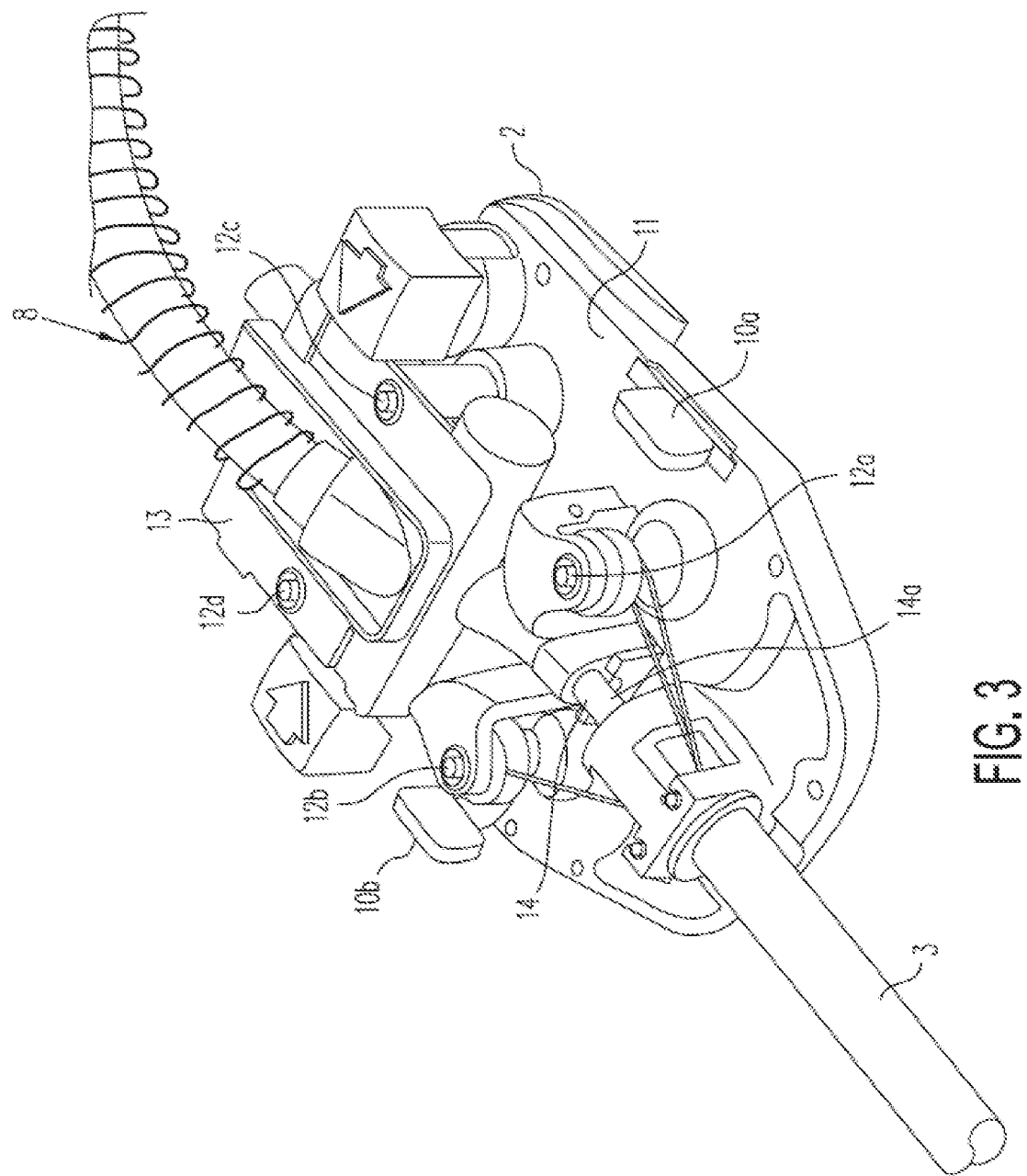
FIG. 3 illustrates a perspective view of a proximal end mechanism according to some embodiments.

FIG. 3 is a perspective view of proximal end mechanism 2 with its protective cover removed, showing certain internal components. FIG. 3 shows a chassis 11 (the reverse side of which is shown in FIG. 2) on which other mechanism 2 components are mounted. According to some embodiments, the reverse side of chassis 11 is coupled to a support platform for holding surgical instrument 1. Four control shafts 12a-12d extend through chassis 11. One end of each shaft 12a,12b is coupled to a unique associated disk 9a,9b and the other end of each shaft 12a,12b coupled to chassis 11. Similarly, one end of each shaft 12c,12d is coupled to a unique associated disk 9c,9d and the other end of each shaft 12c,12d is coupled to valve assembly 13, which in turn is mounted to chassis 11. Transport shaft 3 is also mounted to chassis 11. A small portion 14a of the enclosed channel 14 is shown, which provides a passage for either irrigation or suction between end effector 5 and valve assembly 13. In the depicted embodiment, portion 14a is made of rigid metal but could be other suitable material in other embodiments.

Figure 4:
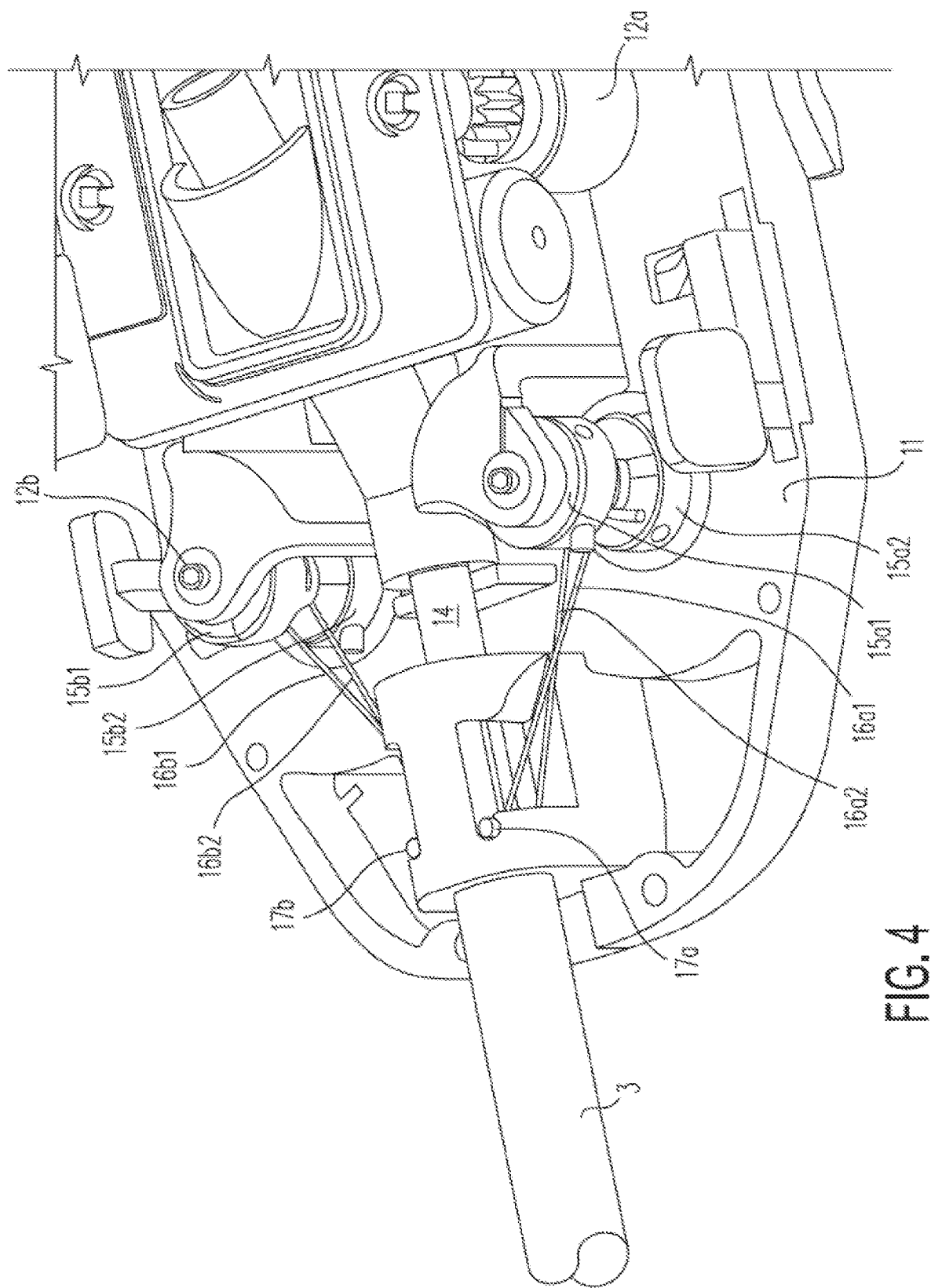
FIG. 4 illustrates a perspective view of wrist orientation control features in a proximal end mechanism according to some embodiments.

FIG. 4 is a perspective view of wrist orientation control features in proximal end mechanism 2. As shown in FIG. 4, two clamping pulleys 15a1, 15a2 are mounted on shaft 12a. A 0.018-inch diameter tungsten cable (tendon) 16a1, 16a2 is wrapped around and secured to each associated unique clamping pulley 15a1,15a2, and the pulleys are secured to shaft 12a so as to maintain tension in the cables. The cables 16a1,16a2 ride over stainless steel pin 17a as they enter the interior of transport shaft 3. In a similar way, two clamping pulleys 15b1, 15b2 are mounted on shaft 12b; cables 16b1, 16b2 are wrapped around and secured to pulleys 15b1, 15b2, and cables 16b1, 16b2 ride over stainless steel pin 17b as they enter transport shaft 3. Pins 17a, 17b provide a sufficient bearing surface for the cables to keep friction concerns within limits for the designed-for life of the instrument, and in other embodiments a material other than stainless steel may be used. Likewise, tungsten provides sufficient strength, wear resistance, and resistance to stretching for the depicted embodiment, although in other embodiments other metal or polymer materials may be used, depending on design requirements.

The wrist control design illustrated in FIG. 4 contains a relatively low number of inexpensive parts, and so enables a relatively lower manufacturing cost in comparison to other designs. For example, U.S. Pat. No. 6,817,974 B2 discloses a gimbal mechanism to control the wrist cables. The embodiment depicted in FIG. 4 is a simple and relatively low cost design that enables the instrument to be disposed after use in a single surgical procedure.

Figure 5:
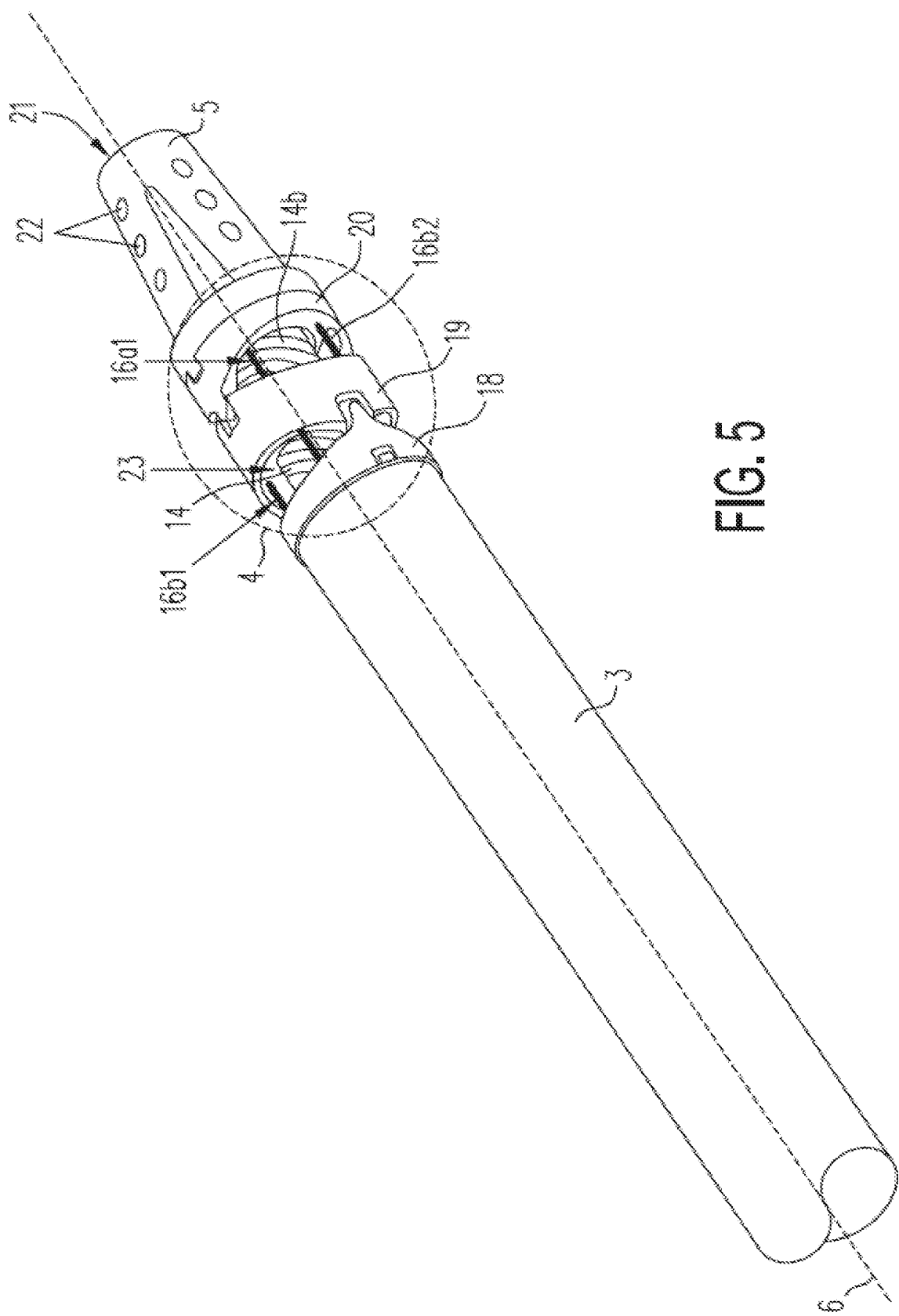
FIG. 5 illustrates a perspective view of a distal end of a surgical instrument including a transport shaft, a wrist mechanism, and an end effector included in the surgical instrument according to some embodiments.

FIG. 5 is a perspective view of the distal end of transport shaft 3, of wrist mechanism 4, and of end effector 5. As shown in FIG. 5, wrist mechanism 4 is a two-stage flexible "snake" design that includes a proximal link 18, a middle link 19, and a distal link 20. Link 18 is coupled to the distal end of transport shaft 3, and end effector 5 is coupled to link 20. The first stage between links 18 and 19 provides a degree of freedom in pitch, and the second stage between links 19 and 20 provides a degree of freedom in yaw (again, these are arbitrary terms). In the depicted embodiment, wrist mechanism 4 is capable of about a 45-degree orientation change in any direction. Three of the four wrist control cables (tendons) 16a1, 16b1, 16a2, 16b2 are visible, and each is routed through links 18 and 19 to be secured to link 20. Each of the tendons 16 may in some embodiments be a single cable, wire, or similar piece, and in other embodiments each of the tendons 16 may be a rigid hypotube (made of, for example, tungsten) to provide rigidity along its length, with cables crimped at the proximal and distal ends for coupling within the proximal end mechanism and the wrist mechanism.

Figure 5A:
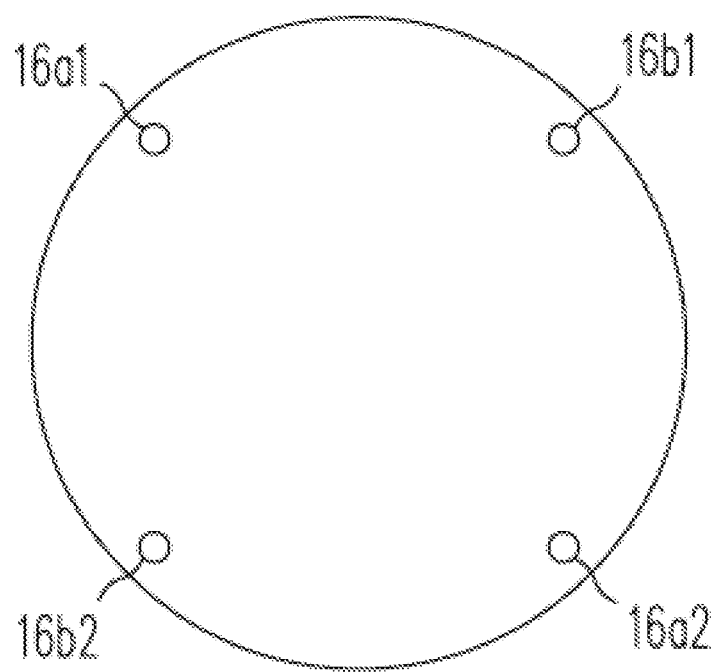
FIG. 5A illustrates a cross-sectional view of a wrist control scheme included in a surgical instrument according to some embodiments.

Referring to FIG. 5A, an embodiment of the wrist control scheme is illustrated. The view is from the distal end looking towards the proximal end, with "pitch" being movement in the 6 to 12 o'clock directions about a "pitch" axis formed by the 3 to 9 o'clock directions. According to FIG. 5A, a "yaw" motion includes movement in the 3 to 9 o'clock directions about a "yaw" axis formed by the 6 to 12 o'clock directions. As shown in FIG. 5A, the cables are positioned symmetrically around the wrist perimeter: cable 16b1 is at about the 1:30 clock position, cable 16a2 is at about the 4:30 clock position, cable 16b2 is at about the 7:30 clock position, and cable 16a1 is at about the 10:30 clock position. Referring to FIG. 4 and its associated description, it can be seen that moving a single input disk 9 does not result in a "pure" pitch or yaw movement. Instead, to produce solely a pitch or yaw motion, both disks 9a and 9b are moved in coordination. Thus the two wrist control inputs are coordinated to provide a desired change in end effect or orientation. This coordinated control movement can be routinely done using known control system programming techniques.

For example, in some embodiments consistent with the present disclosure a pitch motion may be obtained by pulling/pushing, cables 16a1 and 16b1 by the same amount. Even though cables 16a1 and 16b1 have been described above as "tendons," it should be clear that the term is not limiting as to the use of cables or tendons 16a1 and 16b1 for either pushing, or pulling actions. Likewise, a pitch motion may be obtained by pulling/pushing cables 16a2 and 16b2 by the same amount. This configuration may correspond to disks 9a and 9b moving at the same speed, in the same direction. In some embodiments consistent with the present disclosure, a yaw motion may be obtained by pulling/pushing cables 16a1 and 16b2 by the same amount. Likewise, a yaw motion may be obtained by pulling/pushing cables 16a2 and 16b1 by the same amount. This configuration may correspond to disks 9a and 9b moving at the same speed, in opposite directions.

Referring once again to FIG. 5, end effector 5 includes a single center channel 21 and several end effector sidewall holes 22 through to the center channel 21. Center channel 21 is coupled to a coil-reinforced flexible tube 14b (other tubes may be used; tube selection may depend on particular wrist mechanism designs) that is routed through the center of disks 18, 19, and 20 in wrist mechanism 4. Channel 21 is also coupled to another tube (not shown in FIG. 5; see e.g. a proximal end shown in FIG. 3), element 14a at the proximal end of the instrument to provide the suction/irrigation channel 14 through instrument 1. Disks 18, 19, and 20 each have an inner opening (e.g., 0.165 inches) along axis 6, allowing a sufficiently large tube 14b to be used to provide sufficient irrigation and suction for use at the surgical site. Sidewall holes 22 enhance the end effector's suction function.

Figure 5B:
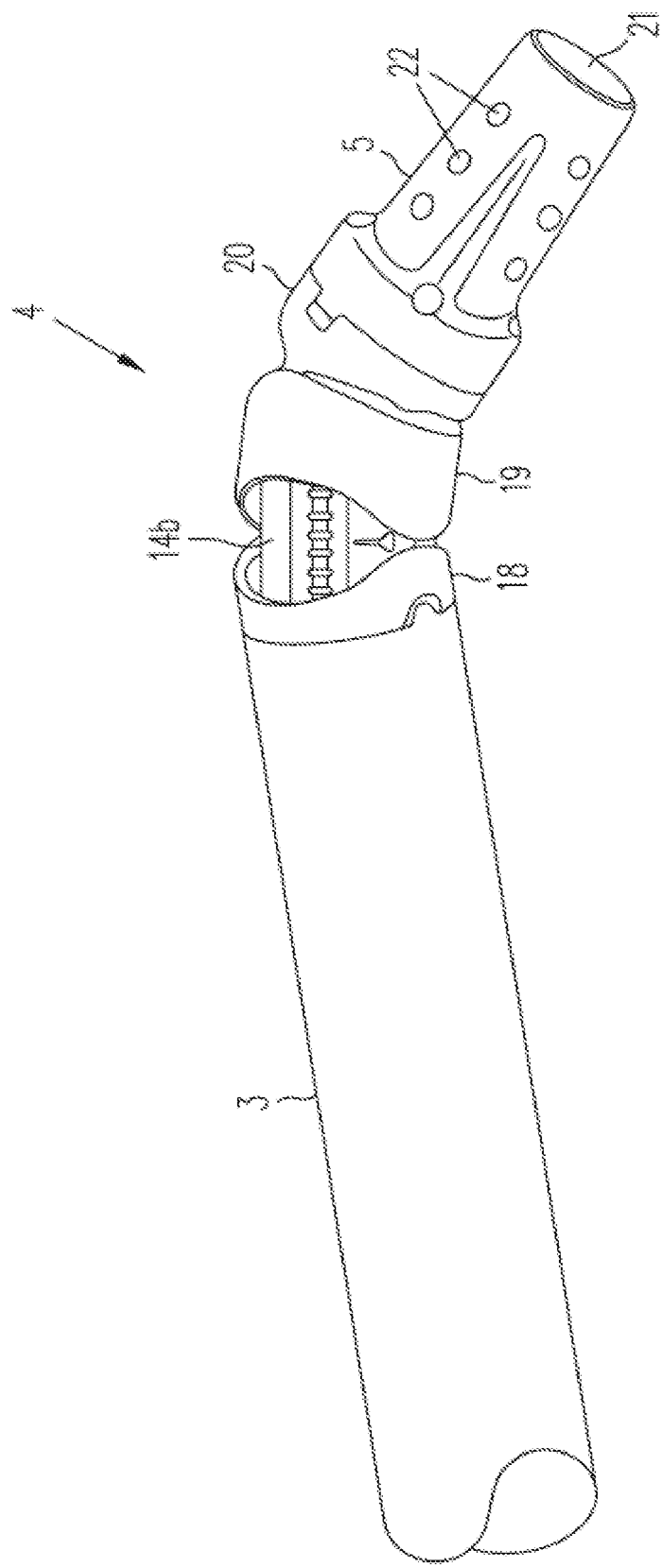
FIG. 5B illustrates a perspective view of a distal end of a transport shaft included in a surgical instrument according to some embodiments.

FIG. 5B is another perspective view of the distal end of transport shaft 3, wrist mechanism 4, and end effector 5. FIG. 5B shows wrist 4 in a flexed position in both pitch and yaw. FIG. 5B also provides a perspective of tube 14b.

Figure 6:
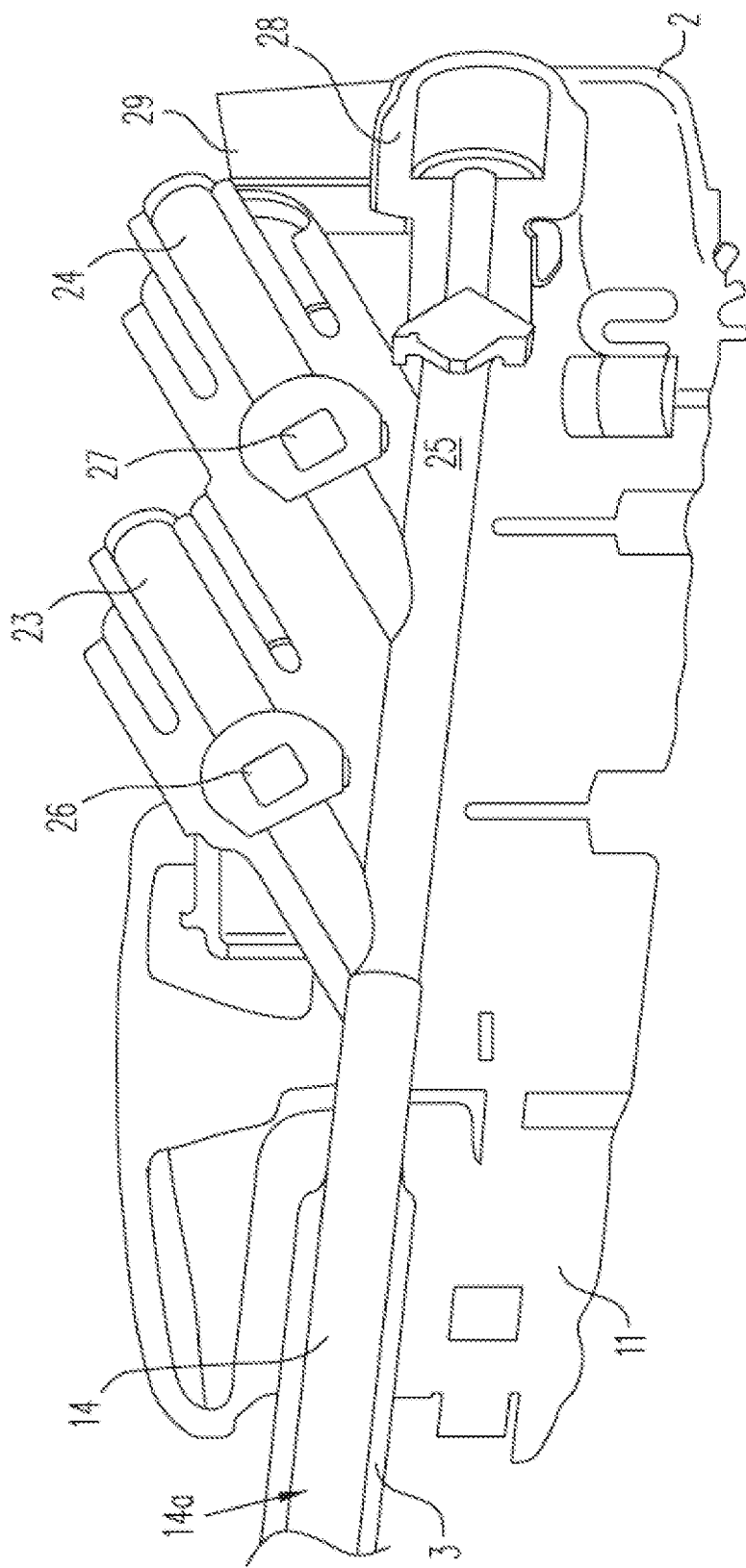
FIG. 6 illustrates a cross-sectional perspective view of a proximal end mechanism and a proximal portion of an instrument including a transport shaft, according to some embodiments.

FIG. 6 is a cross-sectional perspective view of proximal end mechanism 2 and a proximal portion of transport shaft 3, taken along longitudinal axis 6. FIG. 6 shows that irrigation feature channel 23 and suction feature channel 24 both join central channel 14 so that irrigation fluid (e.g., water) can be directed into central channel 14 via irrigation channel 23 and suction material (e.g., insufflation gas, smoke, blood, tissue residue, etc.) can be withdrawn from central channel 14 via suction channel 24. As shown, both feature channels 23, 24 join central channel 14 at about a 30-degree angle, which improves flow rates and reduces clots in the suction channel. In the depicted embodiment, irrigation channel 23 is positioned distal of suction channel 24. In other embodiments the relative positions may be reversed. In addition, in some embodiments either the suction or irrigation channel may be eliminated so that only one of the suction or irrigation functions is provided. FIG. 6 also shows an optional auxiliary channel 25 that joins central channel 14. In the depicted embodiment, auxiliary channel 25 is longitudinally aligned with central channel 14, and in other embodiments channel 25 may be angled with reference to channel 14.

According to embodiments disclosed herein, a plane including an irrigation channel and a suction channel may be perpendicular to a plane S including a side of a surgical instrument adapted to couple to a support platform. For example, the plane including channels 23 and 24 is perpendicular to chassis 11, which forms a side of instrument 1 coupled to provide support, according to some embodiments (see FIG. 6). Such configuration allows for a compact arrangement of a surgical instrument coupled to a robotic manipulator. For example, in surgical instrument 1 connection features 7a and 7b freely extend out when the instrument is placed in a robotic arm; avoiding interference with other parts and components in the robot (see FIG. 1).

Communication between irrigation feature channel 23 and central channel 14 is controlled by movable valve piston 26. Likewise, communication between suction feature channel 24 and central channel 14 is controlled by movable valve piston 27. Access to auxiliary channel 25 is via a removable screw cap 28 and insufflation seal 29. The straight alignment between channel 25 and channel 14 in the depicted embodiment allows a long, thin instrument (not shown) to be inserted into channel 14 for, e.g., cleaning or access to the surgical site through channel 21 in end effector 5. Seal 29 provides a seal around the inserted instrument's shaft. In some embodiments, additional fluid (gas, liquid) may be passed via channel 25 to channel 14 and thence to the surgical site.

Figure 7A:
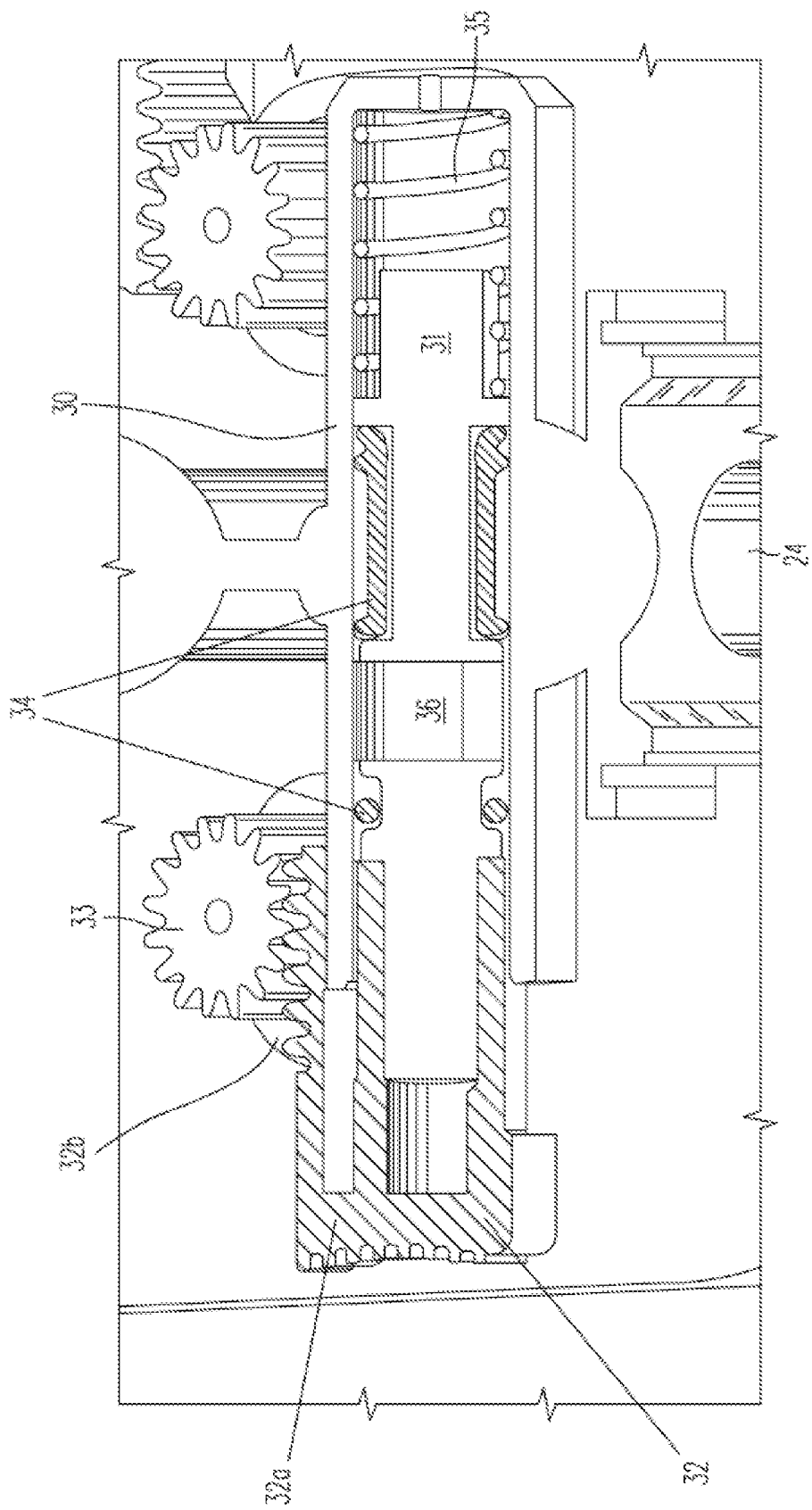
FIG. 7A illustrates a cross-sectional perspective view of a proximal end mechanism included in a surgical instrument according to some embodiments.

FIGS. 7A, 7B, and 7C are cross-sectional perspective views that illustrate valve design and operation. The operation of the suction control valve is shown, and the irrigation control valve is similarly designed. As shown, the suction control valve includes a valve body 30, movable valve member 31, actuation piece 32, and robotic actuation piece 33. In some embodiments, robotic actuation piece 33 is a pinion gear. In the depicted embodiment, the suction control valve is a piston-type valve, although other simple valve designs (e.g., rotary valve with lever actuation) could be used. As depicted, valve body 30 is cylindrical (non-circular cross-sections may be used in other embodiments), and valve member 31 moves linearly inside valve body 30. Seals 34 provide a fluid-tight seal between valve body 30 and valve member 31 as it moves. A coil spring 35 positioned in valve body 30 pushes against valve member 31 to keep valve member 31 in a default closed position, although in alternate embodiments the design may be easily modified to keep the valve member in a default open position, or to eliminate the spring and require positive action (manual or robotic) to move the valve between closed, intermediate, and full open positions. A cross-ways channel 36 in valve member 31 provides an open passage between suction feature channel 24 and central channel 14 when the valve member is moved to an intermediate or full open position.

The movement of valve member 31 may be controlled by either manual or robotic actuation when instrument 1 is mounted on a robotic manipulator. Further, instrument 1 may be removed from the robotic manipulator and manually operated. Thus, instrument 1 is configured to function both as a robotic and a manual instrument, depending on the particular need during a surgical procedure. Actuation piece 32 includes a manual button 32a and a rack gear 32b. Actuation piece 32 is positioned to move valve member 31 inside valve body 30. By pressing on button 32a in the direction of valve member movement, an operator directly moves the valve member. Likewise, motion of rack gear 32b moves the valve member. Combining button 32a and rack gear 32b in a single actuation piece 32 (e.g., a single, unitary structure as shown, although the actuation piece may have several components in other designs) provides a simple way of allowing both manual and mechanical control of the valve member. Skilled artisans will appreciate that other mechanical configurations, such as the use of one or more sector gears, may be used to provide mechanical control in a manner similar to the use of a linear rack and pinion as shown. Nevertheless, the rack and pinion as shown is a space-efficient design that allows one, two, or more such valve actuation mechanisms to be placed in a small space. In addition, the placement of the one or more buttons 32a around the instrument allows single-handed operation of the one or more associated valves, either when the instrument is mounted on the robot or is held in the hand. For example, when mounted on a robot manipulator, the thumb may be used to press on button 32a of one valve with a pinching motion against supporting digits on the other side of the instrument. Similarly, another digit may be used to press on button 32a of another valve with a pinching motion against a supporting thumb on the instrument. Likewise, if the instrument is held in the palm of the hand, the thumb may be used to press on one button 32a and another digit may be used to press on another button 32a.

FIG. 7B illustrates manual operation of surgical instrument 1. During manual actuation, an operator presses (depicted by the arrow P) button 32a, which moves valve member 31 to position channel 36 in at least partial alignment with suction feature channel 24, as shown in FIG. 7B. When the operator releases pressure from button 32a, spring 35 returns valve member 31 towards the closed position, either reducing or stopping the suction flow.

FIG. 7C shows the operation of surgical instrument 1 according to some embodiments consistent with the present disclosure. During robotic (telerobotic) actuation, a servomotor is activated to turn disk 9c, which in turn rotates shaft 12c (see FIGS. 2 and 3). Robotic actuation piece 33 is coupled to shaft 12c, and so rotates with shaft 12c. In the depicted embodiment, actuation piece 33 is a pinion gear that is meshed with rack gear 32b, so that as disk 9c turns, piece 33 exerts a force, (depicted by arrow F), on piece 32. Actuation piece 32 presses on valve member 31 to move it to an intermediate or full open position. The compression force of spring 35 is selected to accommodate the robotic actuation force. It can be seen that robotic actuation piece 33 can be rotated in an opposite direction to move, or to allow spring 35 to move in part or in full, valve member 31 towards a partially or fully closed position.

According to embodiments consistent with the present disclosure, a suction control valve and an irrigation control valve may be linearly actuated valves. Some embodiments may include either a suction control valve or an irrigation control valve, or both a suction control valve and an irrigation control valve being rotationally actuated valves. Furthermore, in some embodiments the actuation axis of an irrigation control valve and a suction control valve may be aligned in a plane parallel to the side S of a proximal end mechanism that mates with a robotic manipulator. This may be side 200 of chassis 11, according to some embodiments disclosed herein (see FIG. 2). This configuration allows for a compact form factor of a surgical instrument as in embodiments disclosed herein. A configuration having irrigation and suction control valves in a plane parallel to the side S may also provide mechanical stability to the surgical robotic manipulator arm assembly. Thus, a surgeon or other personnel may exert a limited amount of torque on the arm assembly while manually operating the suction control valve or the irrigation control valve in a surgical instrument consistent with embodiments disclosed herein. Further according to embodiments disclosed herein, a plane including the actuation axis of an irrigation control valve and a suction control valve may be perpendicular to a plane including an irrigation channel and a suction channel. For example, the plane including piston 26 in an irrigation control valve and piston 27 in a suction control valve is perpendicular to a plane including channels 23 and 24 (see FIG. 6).

Further according to embodiments disclosed herein operation of an irrigation control valve and a suction control valve may be performed independently, either manually, robotically, or by a combination of manual and robotic operation. Thus, in some embodiments turning an irrigation valve "on" may not turn a suction valve automatically "off." Likewise, turning a suction valve "on" may not turn an irrigation valve automatically "off." Furthermore, when an irrigation control valve is turned "off," a suction control valve may remain in an "off" position for a selected amount of time, after which it may be turned "on." The lag time during which an irrigation control valve is "off" and a suction control valve is "off" may be arbitrarily selected by a controller or surgeon, depending on the surgical conditions. Likewise, when a suction valve is turned "off," an irrigation valve may remain in the "off" position for a selected amount of time, chosen by a controller or a surgeon depending on the surgical conditions.

Figure 8:
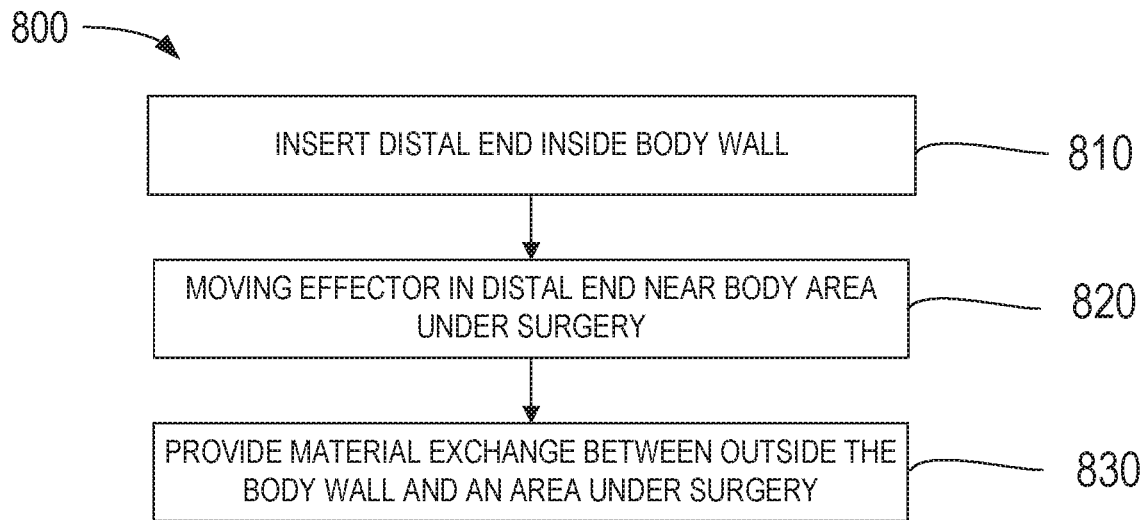
FIG. 8 shows a flowchart of a method to use a surgical instrument according to some embodiments.

FIG. 8 shows a flowchart of a method 800 to use a surgical instrument according to embodiments disclosed herein. Method 800 may be performed manually by personnel in a surgical room, according to embodiments consistent with the present disclosure. In some embodiments, method 800 may be performed by an automated machine being controlled by a surgeon or other personnel. In some embodiments, some steps in method 800 may be performed manually and some steps in method 800 may be performed by an automated machine controlled by a surgeon. For the purpose of illustration, the method shown in FIG. 8 will be discussed in conjunction with FIG. 1. First, a distal end of instrument 1 is inserted inside a body wall of a patient (810). End effector 5 may then be moved in the distal end near a body area under surgery (820) and provide material exchange between outside of the body wall and the area under surgery (830).

According to embodiments consistent with the present disclosure, the surgical instrument used in method 800 may include an end effector at the distal end and an actuator mechanism at the proximal end. The actuator mechanism includes a movable shaft coupled to a tendon and another movable shaft mechanically coupled to a valve. The surgical instrument may further include a transport shaft coupling the actuator mechanism to the end effector. The transport shaft may have a lumen through which a plurality of tendons is coupled between the actuator mechanism and a flexible wrist, allowing control of a pitch and a yaw movement of the end effector. The surgical instrument may further include a channel enclosed in the lumen, the channel providing a cavity coupling the proximal end to the distal end, the cavity having a first aperture coupled to the first valve. Further embodiments of method 800 may include a surgical instrument consistent with surgical instrument 1, described in detail in the present disclosure.

According to embodiments of method 800 consistent with the present disclosure, moving the end effector in the distal end in step 820 may include a motion in a pitch degree of freedom and a motion in a yaw degree of freedom, as well as translating the entire distal end of the instrument along the pitch and yaw planes. In some embodiments of method 800 consistent with the present disclosure, the motion in a pitch degree of freedom includes moving a first movable shaft and a second movable shaft in the actuator mechanism in the same direction, at the same speed; and the motion in a yaw degree of freedom comprises moving the first movable shaft and the second movable shaft in the actuator mechanism in opposite directions, at the same speed.

In embodiments of method 800 consistent with the present disclosure, providing material exchange between outside of the body wall and the area under surgery in step 830 may include actuating the first valve in the actuator mechanism to provide passage of material from outside of the body wall to the area under surgery. Further, in some embodiments step 830 may include actuating a second valve in the actuator mechanism to provide passage of material from the area under surgery to outside of the body wall. According to some embodiments, step 830 may be performed using a manual force or a robotic force. The manual force may be provided by direct contact of a user hand with a proximal end of the instrument.

According to some embodiments, step 830 may include actuating a first valve in a proximal end of the surgical instrument to access a cavity included in a transport shaft of the instrument; wherein actuating the first valve includes actuating an actuator mechanism that includes a robotic control coupled to the first valve and a manual control coupled to the first valve in response to activation of the robotic control or the manual control in a direction perpendicular to a rotational axis of the robotic control.

Further according to some embodiments, step 830 may include coupling a material source to a cavity in the surgical instrument; coupling a suction source to the cavity in the instrument, and actuating a first valve coupled to the cavity to access the material source using an actuator mechanism including a robotic control coupled to the first valve and a manual control coupled to the first valve. Also, step 830 may include actuating a second valve coupled to the cavity to access the suction source using an actuator mechanism including a robotic control coupled to the second valve, and a manual control coupled to the second valve.

Figure 9:
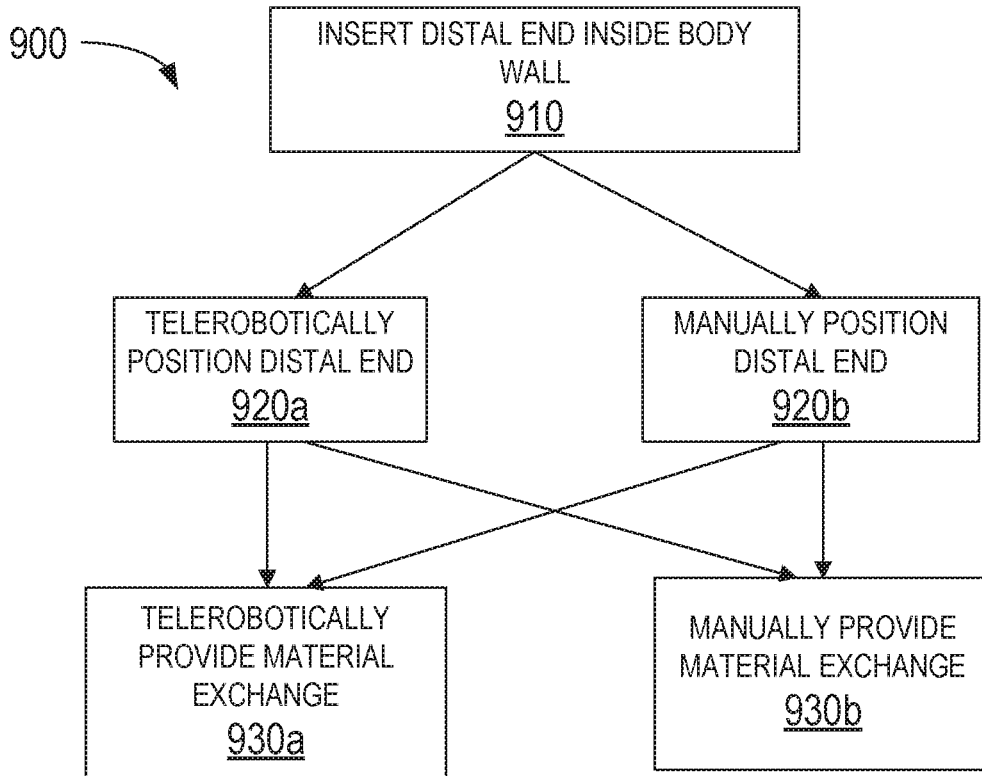
FIG. 9 shows a flowchart of a method to use a surgical instalment according to some embodiments.

FIG. 9 shows a flowchart of a method 900 to use a surgical instrument according to some embodiments. Several operating variations are therefore achieved, as illustrated in FIG. 9. First, in accordance with aspects of the method, a distal end of the instrument may be inserted into a patient, and a proximal end of the instrument mounted to a surgical robotic system manipulator (910). A surgeon may telerobotically operate the instrument and its features. For example, the surgeon may telerobotically position and orient the instrument's end effector, as in step 920a. Furthermore, the surgeon may telerobotically control the suction and irrigation functions to provide material exchange, as in step 930a. Alternatively, while the instrument is mounted to the manipulator, the surgeon may position and orient the instrument's end effector manually, as in step 920b. In some embodiments, the surgeon and a patient side assistant may coordinate operation of the suction and irrigation functions to manually provide material exchange, as in step 930b. Step 930b may be performed by direct contact of a user's hand with the proximal end of the instrument.

For example, while telerobotically operating other surgical instruments at the surgical site, the surgeon may verbally request more or less suction or irrigation, and the patient side assistant may comply by performing step 930b. As another example, the surgeon may telerobotically operate either one of the suction or irrigation features as in 930a, and the patient side assistant may manually operate the other one of the suction or irrigation features as in 930b. The assistant's manual operation overrides the manipulator's commanded valve position, and the valve returns to its commanded position when the assistant releases the valve.

According to some embodiments consistent with the present disclosure, simultaneous suction and irrigation are possible. In such embodiments, teleoperation of a suction control valve and an irrigation control valve may be performed simultaneously. Likewise, manual operation of a suction control valve and an irrigation control valve may be performed simultaneously. Moreover, simultaneous operation of a suction control valve and an irrigation control valve may be performed by a combination of teleoperation of one of the valves and manual operation of the other valve. In some embodiments, the instrument may be removed from the robotic manipulator and the patient side assistant may manually operate the suction and irrigation functions as in 930b.

It is understood that the sequence of steps in FIG. 9 is illustrative only, and different steps may be operated simultaneously or in combination with one another. For example, while a patient side assistant may perform 920b to position the end effector of the instrument, the surgeon may perform 930a for telerobotically irrigate an organ or a tissue with saline solution. Other combinations of steps and procedures consistent with FIG. 9 may be performed according to the present disclosure.

Embodiments disclosed herein are illustrative only and not limiting. One of regular skill in the art may realize that further embodiments consistent with the present disclosure may be provided. The present disclosure is more clearly defined in light of the following claims.

What is claimed is:

1. A method for using a surgical instrument, the method comprising: actuating a movable valve member at a first time during a surgical procedure by using a robotic action; and actuating the movable valve member at a second time during the surgical procedure by using a manual action;
wherein the surgical instrument comprises the movable valve member, a robotic actuation piece, a chassis, a transport shaft coupled to the chassis, a cavity extending through the transport shaft, and a valve;
wherein the chassis comprises a side adapted to be removably mated with a robotic manipulator;
wherein the valve comprises the movable valve member, a manual button coupled to the movable valve member, and a valve channel, the movable valve member being configured to translate across the valve channel along an axis of the movable valve member;
wherein actuating the movable valve member by using the robotic actuation piece comprises rotating the robotic actuation piece around an axis perpendicular to the axis of the movable valve member;
wherein actuating the movable valve member by using the manual action comprises translating the manual button parallel to the axis of the movable valve member; and
wherein the robotic actuation piece is configured to remain engaged with the movable valve member during actuation of the movable valve member by using the manual action.

2. The method of claim 1, further comprising actuating the movable valve member at the second time during the surgical procedure by using the manual action while the chassis is mated to the robotic manipulator.

3. The method of claim 1, further comprising moving an end effector of the surgical instrument by using a robotic action.

4. The method of claim 1, further comprising moving an end effector of the surgical instrument by using a manual action.

5. The method of claim 1, further comprising transporting a material along the transport shaft in response to actuating the movable valve member at the first time or at the second time.

6. The method of claim 5, further comprising directing the material to a point of interest by moving an end effector of the surgical instrument to the point of interest, the end effector being distal to the chassis.

7. The method of claim 5, wherein the material is an irrigation fluid.

8. The method of claim 1, further comprising applying suction to the transport shaft in response to actuating the movable valve member at the first time or at the second time.

9. The method of claim 1, further comprising coupling a material source or a suction source to the cavity.

10. The method of claim 1, wherein:
the surgical instrument further comprises an auxiliary channel defined in the chassis;
the cavity intersects the auxiliary channel;
the cavity and the auxiliary channel together define an axis of the surgical instrument; and
the valve channel intersects the auxiliary channel;
the method further comprising inserting a second surgical instrument into a proximal end of the auxiliary channel, past a distal end of the auxiliary channel, and into the cavity.

11. A method for using a surgical instrument, the method comprising: actuating a movable member of the surgical instrument at a first time during a surgical procedure by using a robotic actuation piece; and
actuating the movable member of the surgical instrument at a second time during the surgical procedure by using a manual action;
wherein the surgical instrument comprises a chassis, the movable member, the robotic actuation piece coupled to the movable member, a manual button coupled to the movable member, a proximal end, and a distal end;
wherein the chassis is at the proximal end of the surgical instrument and comprises a side adapted to be removably mated with a robotic manipulator;
wherein an axis of the surgical instrument is defined by the proximal and distal ends of the surgical instrument, and the movable member of the surgical instrument is configured to translate along an axis of the movable member perpendicular to the axis of the surgical instrument;
wherein actuating the movable member by using the robotic actuation piece comprises rotating the robotic actuation piece around an axis of the robotic actuation piece that is perpendicular to the axis of the movable member; and
wherein actuating the movable member by using the manual action comprises engaging and translating the manual button along the axis of the movable member.

12. The method of claim 11, further comprising actuating the movable member by using the manual action while the chassis is mated to the robotic manipulator.

13. The method of claim 11, further comprising moving an end effector of the surgical instrument, the end effector being located distal to the chassis.

14. The method of claim 13, wherein moving the end effector comprises moving the end effector telerobotically or manually.

15. The method of claim 11, further comprising transporting a material along a transport shaft of the surgical instrument.

16. The method of claim 15, further comprising directing the material to a point of interest by moving an end effector of the surgical instrument to the point of interest, the end effector being distal to the chassis.

17. The method of claim 15, wherein the material is a fluid.

18. The method of claim 11, further comprising applying suction to a transport shaft of the surgical instrument in response to actuating the movable member at the first time or at the second time.

19. The method of claim 11, further comprising coupling a material source or a suction source to a cavity extending through a transport shaft of the surgical instrument.

20. The method of claim 11, further comprising inserting a second surgical instrument into a proximal end of the surgical instrument and past a distal end of chassis.

* * * * *